(12) United States Patent
Grass et al.

(10) Patent No.: US 8,586,784 B2
(45) Date of Patent: Nov. 19, 2013

(54) METHOD FOR CONTINUOUS CATALYTIC HYDROGENATION

(75) Inventors: Michael Grass, Haltern am See (DE); Burkhard Reeken, Dorsten (DE); Axel Tuchlenski, Weinheim (DE); Alfred Kaizik, Marl (DE)

(73) Assignee: Evonik Oxeno GmbH, Marl (DE)

( * ) Notice: Subject to any disclaimer, the term of this patent is extended or adjusted under 35 U.S.C. 154(b) by 2092 days.

(21) Appl. No.: 11/320,409

(22) Filed: Dec. 29, 2005

(65) Prior Publication Data

US 2006/0161017 A1    Jul. 20, 2006

(30) Foreign Application Priority Data

Dec. 31, 2004   (DE) .................. 10 2004 063 673

(51) Int. Cl.
*C07C 61/00*    (2006.01)
(52) U.S. Cl.
USPC ........................................................ 562/509
(58) Field of Classification Search
USPC ........................................................ 562/509
See application file for complete search history.

(56) References Cited

U.S. PATENT DOCUMENTS

| | | | |
|---|---|---|---|
| 3,027,398 A | 3/1962 | Foohey, William L. | |
| 3,636,108 A * | 1/1972 | Brake | 564/450 |
| 5,202,475 A * | 4/1993 | Cook et al. | 562/509 |
| 5,286,898 A * | 2/1994 | Gustafson et al. | 560/127 |
| 5,319,129 A | 6/1994 | Gustafson et al. | |
| 5,578,546 A * | 11/1996 | Maschmeyer et al. | 502/327 |
| 6,015,928 A | 1/2000 | Gubisch et al. | |
| 6,184,424 B1 | 2/2001 | Bueschken et al. | |
| 6,239,318 B1 | 5/2001 | Schuler et al. | |
| 6,284,917 B1 * | 9/2001 | Brunner et al. | 560/127 |
| 6,331,657 B1 | 12/2001 | Kaizik et al. | |
| 6,350,820 B1 * | 2/2002 | Hahnfeld et al. | 525/332.9 |
| 6,403,836 B2 | 6/2002 | Kaizik et al. | |
| 6,407,295 B1 | 6/2002 | Kaizik et al. | |
| 6,482,992 B2 | 11/2002 | Scholz et al. | |
| 6,492,564 B1 | 12/2002 | Wiese et al. | |
| 6,500,991 B2 | 12/2002 | Wiese et al. | |
| 6,555,716 B2 | 4/2003 | Protzmann et al. | |
| 6,570,033 B2 | 5/2003 | Rottger et al. | |
| 6,627,782 B2 | 9/2003 | Kaizik et al. | |
| 6,680,414 B2 | 1/2004 | Knoop et al. | |
| 6,720,457 B2 | 4/2004 | Drees et al. | |
| 6,818,770 B2 | 11/2004 | Selent et al. | |
| 6,924,389 B2 | 8/2005 | Jackstell et al. | |
| 6,956,133 B2 | 10/2005 | Jackstell et al. | |
| 6,960,699 B2 | 11/2005 | Totsch et al. | |
| 7,009,068 B2 | 3/2006 | Schmutzler et al. | |
| 7,109,346 B2 | 9/2006 | Beller et al. | |
| 7,319,161 B2 * | 1/2008 | Noe et al. | 560/127 |
| 7,361,714 B2 * | 4/2008 | Grass et al. | 525/338 |
| 8,455,701 B2 | 6/2013 | Kaizik et al. | |
| 2004/0236133 A1 | 11/2004 | Selent et al. | |
| 2004/0238787 A1 | 12/2004 | Wiese et al. | |
| 2004/0242947 A1 | 12/2004 | Beller et al. | |
| 2005/0043279 A1 | 2/2005 | Selent et al. | |
| 2005/0182277 A1 | 8/2005 | Totsch et al. | |
| 2005/0209489 A1 | 9/2005 | Moller et al. | |
| 2005/0234270 A1 | 10/2005 | Kaizik et al. | |
| 2005/0256281 A1 | 11/2005 | Grund et al. | |
| 2006/0036121 A1 | 2/2006 | Kaizik et al. | |
| 2006/0128998 A1 | 6/2006 | Lueken et al. | |
| 2006/0129004 A1 | 6/2006 | Lueken et al. | |
| 2006/0161017 A1 | 7/2006 | Grass et al. | |
| 2006/0183936 A1 * | 8/2006 | Grass et al. | 560/128 |
| 2006/0241324 A1 | 10/2006 | Moeller et al. | |
| 2011/0060169 A1 | 3/2011 | Kaizik et al. | |
| 2012/0123169 A1 | 5/2012 | Kaizik et al. | |
| 2012/0190895 A1 | 7/2012 | Kaizik et al. | |

FOREIGN PATENT DOCUMENTS

| | | |
|---|---|---|
| DE | 28 23 165 | 11/1979 |
| DE | 10203386 | 7/2003 |
| DE | 102 25 565 | 12/2003 |
| DE | 10225565 | 12/2003 |
| DE | 102 32 868 | 2/2004 |
| WO | 99/32427 | 7/1999 |
| WO | 00/78704 | 12/2000 |
| WO | 2004/009526 | 1/2004 |
| WO | 2004/046078 | 6/2004 |

OTHER PUBLICATIONS

U.S. Appl. No. 12/065,091, filed Feb. 28, 2008, Hess et al.
U.S. Appl. No. 11/574,063, filed Feb. 22, 2007, Nierlich et al.
U.S. Appl. No. 11/494,741, filed Jul. 28, 2006, Kaizik et al.
U.S. Appl. No. 10/562,454, filed Aug. 18, 2006, Krissmann et al.
U.S. Appl. No. 10/576,302, filed Apr. 19, 2006, Kaizik et al.
U.S. Appl. No. 10/588,762, filed Aug. 8, 2006, Wiese et al.
U.S. Appl. No. 10/593,330, filed Sep. 19, 2006, Borgmann et al.
U.S. Appl. No. 10/584,492, filed Jun. 22, 2006, Ortmann et al.
U.S. Appl. No. 10/584,148, filed Jun. 22, 2006, Ortmann et al.

* cited by examiner

*Primary Examiner* — Yevegeny Valenrod
(74) *Attorney, Agent, or Firm* — Oblon, Spivak, McClelland, Maier & Neustadt, L.L.P.

(57) ABSTRACT

The invention relates to the preparation of alicyclic carboxylic acids or their derivatives by selective hydrogenation of the corresponding aromatic carboxylic acid (derivatives) in at least two series-connected reactors, at least one reactor being operated in loop operating mode. The catalyst volumes in the method are set in such a manner that the catalyst volume required, based on the conversion rate, is as low as possible.

14 Claims, 1 Drawing Sheet

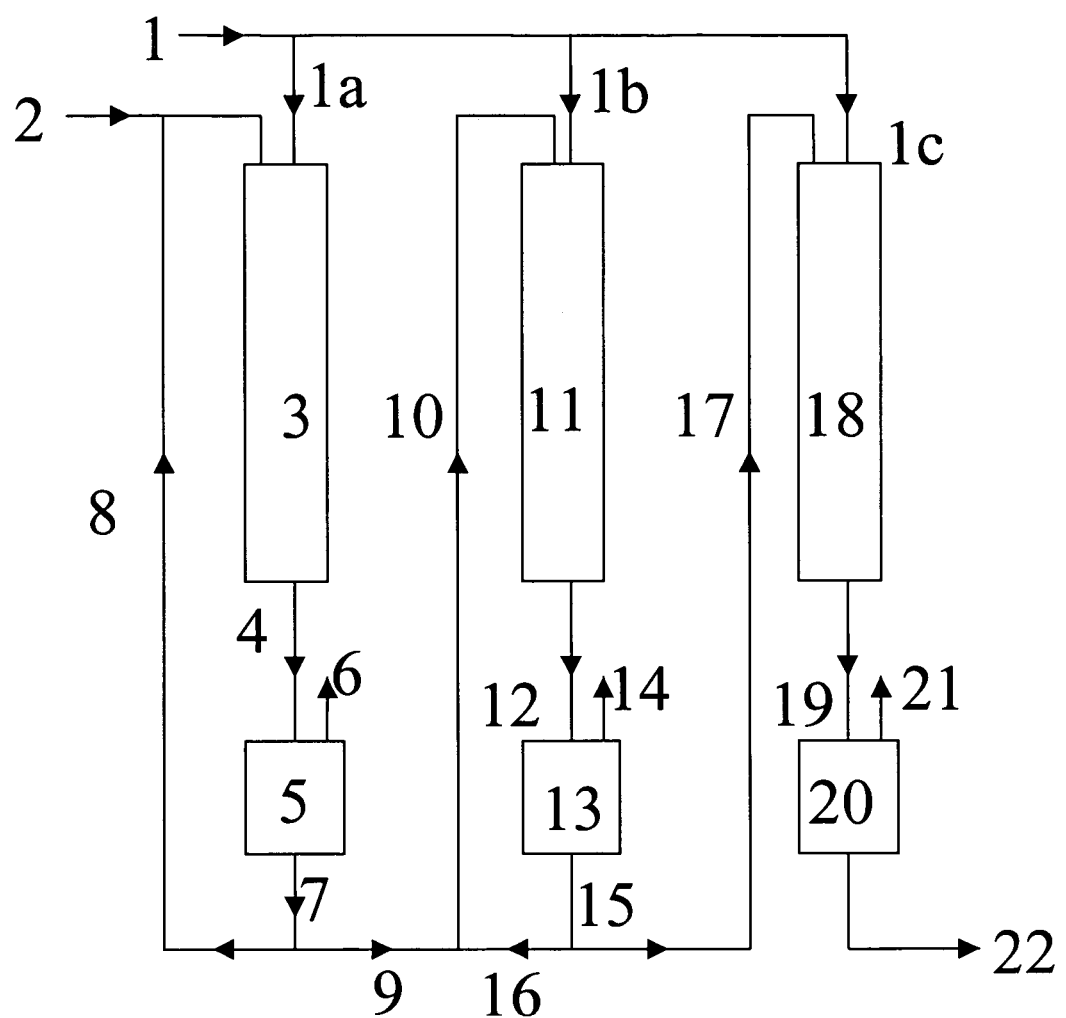

METHOD FOR CONTINUOUS CATALYTIC HYDROGENATION

BACKGROUND OF THE INVENTION

1. Field of the Invention

The invention relates to a method for continuous catalytic hydrogenation, and in particular a method for preparing alicyclic carboxylic acids or their derivatives, in particular carboxylic esters, by selective hydrogenation of the corresponding aromatic carboxylic acid(s) (derivatives) in at least three series-connected reactors, at least the two first being operated in the loop operating mode.

2. Description of the Background

Alicyclic polycarboxylic esters, for example the esters of cyclohexane-1,2-dicarboxylic acid, are used as lubricating oil components and as aids in metal processing. In addition, they are used as plasticizers for polyolefins and PVC.

For plasticizing PVC, predominantly use is made of esters of phthalic acid, for example dibutyl, dioctyl, dinonyl or didecyl esters of phthalic acid. Since the use of these phthalates is increasingly under discussion in recent time as controversial, their use in plastics could be restricted. Alicyclic polycarboxylic esters, of which some are already described in the literature as plasticizers for plastics could then be used as suitable substitutes.

In most cases, the most economical route for preparing alicyclic polycarboxylic esters is nuclear hydrogenation of the corresponding aromatic polycarboxylic esters, for example of the abovementioned phthalates. Some methods are already known for this:

In U.S. Pat. Nos. 5,286,898 and 5,319,129, methods are described by which dimethyl terephthalate can be hydrogenated in the presence of supported Pd catalysts which are doped with Ni, Pt and/or Ru at temperatures greater than or equal to 140° C. and at a pressure between 50 and 170 bar to give the corresponding hexahydrodimethyl terephthalate.

U.S. Pat. No. 3,027,398 discloses the hydrogenation of dimethyl terephthalate in the presence of supported Ru catalysts at 110 to 140° C. and 35 to 105 bar.

In DE 28 23 165, aromatic carboxylic esters are hydrogenated to the corresponding alicyclic carboxylic esters in the presence of supported Ni, Ru, Rh and/or Pd catalysts at 70 to 250° C. and 30 to 200 bar. In this case use is made of a macroporous support having a mean pore size of 70 nm and a BET surface area of approximately 30 m²/g.

Further supported ruthenium catalysts for preparing alicyclic polycarboxylic esters by hydrogenating aromatic polycarboxylic esters are claimed in the patent documents WO 99/32427, WO 00/78704, DE 102 25 565.2 and DE 102 32 868.4.

WO 2004/046078 describes the hydrogenation of benzenepolycarboxylic acids or their derivatives in the presence of a catalyst which has the active catalyst metal applied on a support, the one or more materials having ordered mesopores.

The aromatic polycarboxylic esters are hydrogenated in U.S. Pat. No. 3,027,398 batchwise, in U.S. Pat. Nos. 5,286,898, 5,319,129, DE 28 23 165, WO 99/32427 and WO 00/78704 continuously in a tubular reactor without or with recirculation (loop operating mode) of the hydrogenation output.

In DE 102 32 868.4 and DE 102 25 565.2, the aromatic polycarboxylic esters are hydrogenated to the corresponding alicyclic polycarboxylic esters in two series-connected reactors, the first being operated in loop operating mode (partial recirculation of the reactor output) and the second being operated in straight through-flow passage. The first loop reactor can also be replaced by a plurality of small series- or parallel-connected loop reactors, these reactors having a shared circuit.

The technically known methods are not completely satisfactory with respect to the space-time yield and/or the selectivity. In addition, relatively large amounts of catalyst are required. It was an object of the present invention, therefore, to provide a hydrogenation method which can be carried out with as little catalyst as possible relative to the conversion rate to be achieved.

It has now been found that the required catalyst volume in the hydrogenation, in particular in the nuclear hydrogenation of aromatic carboxylic esters to the corresponding alicyclic carboxylic esters, can be minimized when the hydrogenation is carried out in at least three series-connected hydrogenation units, at least the two first hydrogenation units being operated in loop operating mode, i.e. with recirculation of a part of the respective hydrogenation output and with use of defined catalyst volumes in the individual hydrogenation units.

SUMMARY OF THE INVENTION

The invention relates to a method for continuous catalytic hydrogenation, and in particular a method for preparing alicyclic carboxylic acids or their derivatives, in particular carboxylic esters, by selective hydrogenation of the corresponding aromatic carboxylic acid(s) (derivatives) in at least three series-connected reactors, at least the two first being operated in the loop operating mode.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 shows a block diagram of an embodiment of the inventive method.

DETAILED DESCRIPTION OF THE INVENTION

A method for the continuous catalytic hydrogenation of at least one hydrogenatable compound using a hydrogenation gas in the presence of at least one solid catalyst disposed in a fixed bed, which comprises: carrying out the hydrogenation in at least two series-connected hydrogenation units and operating at least one of the two hydrogenation units in loop operating mode, with, in the hydrogenation units, catalyst volumes being used which deviate by a maximum of 20% from the catalyst volumes which are obtained by a process which comprises a) determining the kinetics of the hydrogenation to be carried out, b) calculating the required catalyst volume for the reactor types used for preset reactor input and output concentrations, c) determining the required total catalyst volume by combining the calculated catalyst volumes, in each case only those combinations being performed which lead to the desired end concentration of the starting material to be hydrogenated used, d) preparing a curve from the total catalyst volumes determined in c) plotted against the conversion rate, e) determining the minimum of the curve prepared in d) and f) determining the catalyst volumes, of the individual hydrogenation units, to be assigned to the minimum.

A hydrogenation unit here and in the text hereinafter, is taken to mean a hydrogenation reactor, or a plurality of series-connected reactors, or a plurality of parallel-connected reactors, or a reactor group which consists of parallel- and series-connected reactors, that is to say a reactor or a reactor arrangement which can exercise the function of a reactor in the inventive method.

A hydrogenatable compound here and in the text hereinafter, is taken to mean a compound that is capable of being hydrogenated.

A hydrogenation gas here and in the text hereinafter, is taken to mean a gas comprising hydrogen ($H_2$).

The inventive method has the advantage that the catalyst volume to be used in hydrogenation reactions can be minimized in relation to the conversion rate. In this manner, the procurement costs for replacement packings of catalyst and also the reactor size can be restricted to that which is necessary.

By means of the simple series connection of at least two loop reactors, the space-time yield, compared with the methods described in the prior art, can furthermore be increased. By means of the presence of a plurality of loop reactors, furthermore, a higher security against breakdown, simpler maintenance and longer service lives can be achieved.

The inventive method is described by way of example hereinafter without the intention of limiting the invention to the exemplary embodiments. Where hereinafter ranges, general formulae or classes of compounds are specified, these are intended not only to comprise the corresponding ranges or groups of compounds which are explicitly mentioned, but also all partial ranges and partial groups of compounds which can be obtained by omitting individual values (ranges) or compounds.

The inventive method for continuous catalytic hydrogenation of hydrogenatable compounds using a hydrogen-containing gas in the presence of solid catalysts disposed in a fixed bed is distinguished by the fact that the hydrogenation is carried out in at least two series-connected hydrogenation units, and that at least one of the two hydrogenation units is operated in loop operating mode, with, in the hydrogenation units, catalyst volumes being used which deviate by a maximum of 20%, preferably by a maximum of 10%, more preferably by a maximum of 5%, and most preferably by a maximum of 2%, from the catalyst volumes which are obtained by a process which comprises a) determining the kinetics of the hydrogenation to be carried out, b) calculating the required catalyst volume for the reactor types used for preset reactor input and output concentrations, c) determining the required total catalyst volume by combining the calculated catalyst volumes, in each case only those combinations being performed which lead to the desired end concentration of the starting material to be hydrogenated used, d) preparing a curve from the total catalyst volumes determined in c) plotted against the conversion rate, e) determining the minimum of the curve prepared in d) and f) determining the catalyst volumes, of the individual hydrogenation units, to be assigned to the minimum.

By carrying out the method using the catalyst volumes thus calculated, the required catalyst volume relative to the conversion rate can be kept as low as possible.

The kinetics of the hydrogenation to be carried out can be determined by all conceivable methods known to those skilled in the art. Preferably, first the catalyst to be used for the hydrogenation under consideration is established. Suitable catalysts can be found in the prior art, or can be determined by catalyst selection (catalyst screening), e.g. by high throughput methods.

After selection of the catalysts, experiments are carried out for determining the reaction rate, with the physical parameters affecting the reaction rate, for example temperature, pressure, concentration (at the start of the reaction) and LHSV (volumetric flow rate of starting material based on catalyst volume) being varied. The number of experiments to be carried out is given by statistical Design of Experiments (DoE).

On the basis of the data determined by the experiments, using evaluation software the data are fitted to a kinetic model which describes all relevant reactions and side reactions in the reaction chamber and takes into account the real temperature and pressure dependencies. As evaluation software, use can be made of, for example, the software package Presto-Kinetics from Dr. Michael Wulkow Computing in Technology GmbH (CiT), Oldenburger Str. 200, D-26180 Rastede, Germany. For the respective kinetic model, the relevant parameters and constants, for example order of reaction, rate constant and activation energy are specified and optimized by the evaluation software. The fitting can be considered to be completed when the deviation (residuum) between model and the data actually determined is less than 20%, preferably less than 10%, more preferably less than 7.5%, and most preferably less than 5%. If, during the optimization/fitting, only relatively large deviations are achieved, the model must be appropriately adapted. If appropriate, further data necessary for the model must be generated by further experiments. Depending on the reaction system under consideration, adsorption constants and/or further parameters (pressure-dependent gas solubilities or the like) can be obtained or be necessary.

Using the kinetics thus obtained, in step b) the catalyst volume required for the reactor types contemplated for use can be calculated for preset reactor input and output concentrations for the reactors used (and thus a defined or preset conversion rate), with otherwise constant parameters (temperature, pressure etc.). The calculation can in turn be performed using the software package Presto-Kinetics. Reactor types which come into consideration are all customary reactor types, for example tubular reactors, circulation reactors and stirred tanks, and also cascades of reactor types.

On the basis of the catalyst volumes calculated according to b), by logical combination of the individual volumes, with in each case only those combinations being used which lead to the desired end concentration of the starting material to be hydrogenated used, a required total catalyst volume can be determined (step c)). The total catalyst volume is given by addition of the individual volumes.

In the next step d), from the total catalyst volumes determined in c) plotted against the conversion rate, a curve is determined. By determining the minimum of the curve in step e), which can be performed graphically or in a program-supported manner, the optimum total catalyst volume can be determined.

From the total catalyst volume for the point in the minimum, in step f), the corresponding apportionment of the catalyst volume among the participating reactors can be taken. Via the respective catalyst volumes determined, the optimum associated residence time can be determined. Residence times are taken to mean in the context of the present invention mean residence times (reciprocal LHSV). These are defined as the quotient of the given reaction volume or of the bulk volume of the catalyst (is often identical in the case of heterogeneous reaction systems), and the total volumetric flow rate (without recycle stream) of the starting material (of the starting material to be hydrogenated).

Hereinafter, the procedure of step b) is to be described by way of example with reference to a 3-stage method (two loop reactors and one tubular reactor in the straight through-flow passage) for nuclear hydrogenation of diisononyl phthalates (DINP), without the inventive method being intended to be limited to this embodiment. For the first reaction stage (loop reactor), at a fixed inlet concentration (100% by mass DINP), the end concentration was varied and the dependent catalyst volumes were calculated. For the second reaction stage (second loop reactor), for a fixed end concentration (5% by mass DJNP), the dependent catalyst volume was calculated for the varying inlet concentrations. The catalyst volume for the third reaction stage (tubular reactor in the straight through-flow passage for finishing hydrogenation), the maximum conversion rate was limited to 5% owing to side conditions such as exothermy in order to be able to implement an adiabatic mode of operation. In a circulation reactor, the catalyst volume resulting from the kinetics is a function of the inlet concentration and the conversion rate. The results of carrying out the fitting of the model can be taken from Example 1.

The ratio of the residence times in the series-connected loop reactors in the inventive method is preferably from 0.01 to less than 1, preferably from 0.1 to 0.9, and most preferably from 0.2 to 0.5. The residence times are preferably set in such a manner that, in the first of the series-connected loop reactors, a conversion rate of from 40 to 90%, preferably from 60 to 90%, are achieved and in the second loop reactor, a conversion rate of from 2 to 60%, preferably from 5 to 40%, is achieved, based on the starting concentration of the compound to be hydrogenated at the inlet of the respective reactor.

It can be advantageous if all hydrogenation units in the inventive method are operated in loop operating mode. Likewise, it can be advantageous if the last hydrogenation unit is operated in straight through-flow passage. The inventive method of hydrogenation can be carried out in an apparatus which has exactly two hydrogenation units or which has more than two hydrogenation units. Preferably, the inventive method is carried out in an apparatus which has three hydrogenation units.

A variant of the inventive method having three hydrogenation units is shown as block diagram in FIG. 1. It must be emphasized that the variant shown here also applies mutatis mutandis to methods having more than three hydrogenation units. In the embodiment of the invention shown in FIG. 1, the first two hydrogenation units are operated in the loop operating mode and the third hydrogenation unit is operated in the straight through-flow passage. Other embodiments are possible in which all three hydrogenation units are operated in loop operating mode, or in which more than three hydrogenation units are present. If the hydrogenation is carried out in a hydrogenation plant having more than three hydrogenation units, according to the invention, the first two hydrogenation units are operated in loop operating mode and the following hydrogenation units can optionally be operated in loop operating mode or in straight through-flow passage.

In the variant of the inventive method shown in FIG. 1, each individual reactor is charged with hydrogenation gas. In order to minimize hydrogen consumption and the output losses caused by the offgas streams, it can be expedient to use the offgas of one hydrogenation unit as hydrogenation gas for another hydrogenation unit. For example, in a method as shown in FIG. 1, the offgas (6) from the first hydrogenation unit (3) can be fed into the second hydrogenation unit (11) instead of the hydrogenation gas (1b), and the offgas (14) of the second hydrogenation unit (11) can be fed into the third hydrogenation unit (18) instead of the hydrogenation gas (1c). In this case, liquid starting material/product phase and hydrogenation gas flow in the same sequence through the reactors. Likewise, it can be expedient to allow hydrogenation gas and starting material/product phase to flow through the reactors in opposite direction. In this case, fresh hydrogenation gas is introduced into the last reactor and offgas from the first reactor is discharged. Furthermore, two or more reactors can have a shared hydrogenation gas system and other reactors can be charged separately therefrom with hydrogenation gas. When the offgas of one reactor is used as hydrogenation gas of another reactor, if desired, the pressure drop can be compensated for by intermediate compression.

Preferably, the offgas quantities and gas streams are set in such a manner that in all reactors good fluid dynamics is present. Good fluid dynamic is distinguished by low wall flow, a high interfacial area for mass transfer and/or pulse-flow.

As hydrogenation gases, use can be made of any desired hydrogen-containing gas mixtures which do not comprise harmful amounts of catalyst poisons, for example carbon monoxide or hydrogen sulfide. The use of inert gases is optional, preferably, hydrogen at a purity greater than 95%, in more greater than 98%, is used. Inert gas fractions can be, for example, nitrogen or methane. Preferably, sufficient hydrogen is present in the hydrogenation units so that it is present in excess, in particular in an excess of 200%, preferably in an excess of from 5 to 100%, and more preferably in an excess of from 10 to 50%, based on the stoichiometric amount which is required to achieve the conversion rate which is possible or desired in the hydrogenation unit. Without setting a sufficient excess of hydrogen, the hydrogenation of the aromatic bonds is achieved only incompletely, which leads to losses of yield.

As hydrogenatable compounds, use can be made in the inventive method of all unsaturated organic compounds. Preferably, as compounds to be hydrogenated in the inventive method, use is made of aliphatically or aromatically unsaturated compounds. Preferably, in the inventive method, as hydrogenatable compounds, use is made of aromatic carboxylic acids or their derivatives which are nuclear-hydrogenated.

In the inventive method, in particular, an aromatic carboxylic acid or a derivative thereof or a mixture of aromatic carboxylic acids or their derivatives can be hydrogenated in the liquid phase or liquid/gas mixed phase, with hydrogen to the corresponding alicyclic carboxylic acid(s) or derivatives thereof in at least three series-connected hydrogenation units continuously in the presence of a catalyst disposed in a fixed bed.

By means of the inventive method, aromatic carboxylic acids or their derivatives, such as aromatic mono-, di- or polycarboxylic acids or their derivatives, for example their esters or anhydrides, in particular their alkyl esters, can be reacted to give the corresponding alicyclic carboxylic acid compounds. As aromatic di- or polycarboxylic acid derivatives, not only full esters, but also partial esters can be hydrogenated using the inventive method. Full ester is intended to mean a compound in which all acid groups are esterified. Partial esters are compounds having at least one free acid group (or if appropriate one anhydride group) and at least one ester group. If polycarboxylic esters are used in the inventive method, these preferably comprise 2, 3 or 4 ester functions.

In the inventive method, as aromatic di- or polycarboxylic acids or their derivatives, use is preferably made of benzene-, diphenyl-, naphthalene-, diphenyl oxide- or anthracene-polycarboxylic acids, their anhydrides and/or the corresponding esters. The alicyclic di- or polycarboxylic acids or their derivatives obtained by the inventive method consist of one or more $C_6$ rings, if appropriate linked by a C—C bond, or fused.

In a preferred embodiment, the present invention relates to a method for hydrogenating 1,2-, 1,3- or 1,4-benzenedicarboxylic acid or derivatives thereof, in particular esters thereof, and/or 1,2,3-, 1,2,4- or 1,3,5-benzenetricarboxylic acid or derivatives thereof, in particular esters thereof, i.e. the isomers of 1,2-, 1,3- or 1,4-cyclohexanedicarboxylic acid or derivatives thereof, in particular esters thereof, or 1,2,3-, 1,3,5- or 1,2,4-cyclohexanetricarboxylic acid or derivatives thereof, in particular esters thereof are obtained.

In the inventive method, for example, the following aromatic carboxylic acids or derivatives thereof, in particular esters, can be used: 1,2-naphthalenedicarboxylic acid, 1,3-naphthalenedicarboxylic acid, 1,4-naphthalenedicarboxylic acid, 1,5-naphthalenedicarboxylic acid, 1,6-naphthalenedicarboxylic acid, 1,7-naphthalenedicarboxylic acid, 1,8-naphthalene-dicarboxylic acid, phthalic acid (benzene-1,2-dicarboxylic acid), isophthalic acid (benzene-1,3-dicarboxylic acid), terephthalic acid (benzene-1,4-dicarboxylic acid), benzene-1,2,3-tri-carboxylic acid, benzene-1,2,4-tricarboxylic acid (trimellitic acid), benzene-1,3,5-tricarboxylic acid (trimesic acid), benzene-1,2,3,4-tetracarboxylic acid. In addition, use can be made of acids or their derivatives, in particular esters, which are formed from said acids by substitution by alkyl, cycloalkyl or alkoxyalkyl groups of one or more hydrogen atoms bound to the aromatic nucleus.

As aromatic monocarboxylic acids or their derivatives, use can be made in the inventive method of, e.g. benzoic acid, 1-naphthoic acid or 2-naphthoic acid or their derivatives, in particular their esters. Furthermore, use can be made of monocarboxylic acids or their derivatives, in particular esters, which are formed from said monocarboxylic acids by substitution by alkyl, cycloalkyl or alkoxyalkyl groups of one or more hydrogen atoms bound to the aromatic nucleus.

Particularly preferably, use can be made in the inventive method of the aromatic carboxylic esters of the abovementioned aromatic carboxylic acids. The alcohol component of the aromatic carboxylic esters preferably used preferably consists of branched or linear (unbranched) alkyl, cycloalkyl or alkoxyalkyl groups having 1 to 25 carbon atoms, preferably 3 to 15, more preferably 8 to 13, carbon atoms, and most preferably 9 or 10 carbon atoms. The alcohol component can have one or more hydroxyl groups. If more than one carboxyl group is present in a molecule, the alcohol components in a molecule of an aromatic polycarboxylic ester used can be identical or different, i.e. they can have identical or different isomers or chain lengths. Obviously, isomers with respect to the substitution pattern of the aromatic system can also be used in the form of a mixture, e.g. a mixture of phthalic ester and terephthalic ester.

In the inventive method, as ester of an aromatic di- or polycarboxylic acid, use can be made of, for example the following compounds: terephthalic acid monomethyl ester, terephthalic acid dimethyl ester, terephthalic acid diethyl ester, terephthalic acid di-n-propyl ester, terephthalic acid dibutyl ester, terephthalic acid diisobutyl ester, terephthalic acid di-tert-butyl ester, terephthalic acid monoglycol ester, terephthalic acid diglycol ester, terephthalic acid diisoheptyl ester, terephthalic acid n-octyl ester, terephthalic acid diisooctyl ester, terephthalic acid di-2-ethylhexyl ester, terephthalic acid di-n-nonyl ester, terephthalic acid diisononyl ester, terephthalic acid di-n-decyl ester, terephthalic acid diisodecyl ester, terephthalic acid dipropylheptyl ester, terephthalic acid di-n-undecyl ester, terephthalic acid diisododecyl ester, terephthalic acid ditridecyl ester, terephthalic acid di-n-octadecyl ester, terephthalic acid diisooctadecyl ester, terephthalic acid di-n-eicosyl ester, terephthalic acid monocyclohexyl ester; phthalic acid monomethyl ester, phthalic acid dimethyl ester, phthalic acid di-n-propyl ester, phthalic acid di-n-butyl ester, phthalic acid diisobutyl ester, phthalic acid di-tert-butyl ester, phthalic acid monoglycol ester, phthalic acid diglycol ester, phthalic acid diisoheptyl ester, phthalic acid di-n-octyl ester, phthalic acid diisooctyl ester, phthalic acid diethylhexyl ester, phthalic acid di-n-nonyl ester, phthalic acid diisononyl ester, phthalic acid di-n-decyl ester, phthalic acid di-2-propylheptyl ester, phthalic acid diisodecyl ester, phthalic acid di-n-undecyl ester, phthalic acid diisoundecyl ester, phthalic acid ditridecyl ester, phthalic acid di-n-octadecyl ester, phthalic acid diisooctadecyl ester, phthalic acid di-n-eicosyl ester, phthalic acid monocyclohexyl ester; phthalic acid dicyclohexyl ester, isophthalic acid monomethyl ester, isophthalic acid dimethyl ester, isophthalic acid dimethyl ester, isophthalic acid diethyl ester, isophthalic acid di-n-propyl ester, isophthalic acid di-n-butyl ester, isophthalic acid diisobutyl ester, isophthalic acid di-tert-butyl ester, isophthalic acid monoglycol ester, isophthalic acid diglycol ester, isophthalic acid diisoheptyl ester, isophthalic acid di-n-octyl ester, isophthalic acid diisooctyl ester, isophthalic acid di-2-ethylhexyl ester, isophthalic acid di-n-nonyl ester, isophthalic acid diisononyl ester, isophthalic acid di-n-decyl ester, isophthalic acid diisodecyl ester, isophthalic acid dipropylheptyl ester, isophthalic acid di-n-undecyl ester, isophthalic acid diisododecyl ester, isophthalic acid di-n-dodecyl ester, isophthalic acid ditridecyl ester, isophthalic acid di-n-octadecyl ester, isophthalic acid diisooctadecyl ester, isophthalic acid di-n-eicosyl ester, isophthalic acid monocyclohexyl ester. As aromatic dicarboxylic acid derivative, very particularly preferably, use is made of diisononyl phthalate or didecyl phthalate.

In the inventive method, as ester of the monocarboxylic acids, use can be made of, e.g. benzoates of diols, for example glycol dibenzoate, diethylene glycol dibenzoate, triethylene glycol dibenzoate or dipropylene glycol dibenzoate, or else benzoic acid alkyl ester, for example decyl or isodecyl benzoate, nonyl or isononyl benzoate, octyl or isooctyl benzoate, 2-ethylhexyl benzoate or tridecyl or isotridecyl benzoate. As aromatic monocarboxylic acid derivative, use can be made particularly preferably of isononyl benzoate or decyl benzoate.

In the inventive method, use can also be made of mixtures of two or more carboxylic acids or carboxylic acid derivatives, in particular mixtures of carboxylic esters. Such mixtures can be obtained, for example, in the following ways:

a) a di- or polycarboxylic acid is partially esterified with an alcohol in such a manner that full and partial esters are present simultaneously.

b) a mixture of at least two carboxylic acids is esterified with an alcohol, a mixture of at least two full esters being formed.

c) a di- or polycarboxylic acid is esterified with an alcohol mixture, in which case a corresponding mixture of full esters can be formed.

d) a di- or polycarboxylic acid is partially esterified with an alcohol mixture.

e) a mixture of at least two carboxylic acids is partially esterified with an alcohol mixture.

f) a mixture of at least two di- or polycarboxylic acids is partially esterified with an alcohol mixture.

In these reactions, instead of the polycarboxylic acids, the corresponding anhydrides can also be used.

On a large scale, aromatic esters, in particular the full esters, are prepared by route c) frequently from alcohol mixtures. Corresponding alcohol mixtures are, for example:

$C_5$-alcohol mixtures, prepared from linear butenes by hydroformylation and subsequent hydrogenation;

$C_5$-alcohol mixtures, prepared from isobutene or butene mixtures which comprise linear butenes and isobutene, by hydroformylation and subsequent hydrogenation;

$C_6$-alcohol mixtures, prepared from a pentene or a mixture of two or more pentenes, by hydroformylation and subsequent hydrogenation;

C$_7$-alcohol mixtures, prepared from triethylene or dipropene or a hexene isomer or another mixture of hexene isomers by hydroformylation and subsequent hydrogenation;

C$_8$-alcohol mixtures, such as 2-ethylhexanol (2 isomers), prepared by aldol condensation of n-butyraldehyde and subsequent hydrogenation;

C$_9$-alcohol mixtures, prepared from C$_4$-olefins by dimerization, hydroformylation and hydrogenation. For preparation of the C$_9$-alcohols, starting materials which can be used are isobutene or a mixture of linear butenes or mixtures with linear butenes and isobutene. The C$_4$-olefins can be dimerized using different catalysts, for example proton acids, zeolites, organometallic nickel compounds or solid nickel-containing contact catalysts. The C$_8$-olefin mixtures can be hydroformylated using rhodium or cobalt catalysts. There is therefore a multiplicity of technical C$_9$-alcohol mixtures.

C$_{10}$-alcohol mixtures prepared from tripropylene by hydroformylation and subsequent hydrogenation; 2-propylheptanol (2 isomers), prepared by aldol condensation of valeraldehyde and subsequent hydrogenation;

C$_{10}$-alcohol mixtures, prepared from a mixture of at least two C$_5$-aldehydes by aldol condensation and subsequent hydrogenation;

C$_{13}$-alcohol mixtures, prepared from dihexene, hexaethylene, tetrapropylene or tributene by hydroformylation and subsequent hydrogenation.

Further alcohol mixtures can be produced by hydroformylation and subsequent hydrogenation from olefins or olefin mixtures which arise, for example, in Fischer-Tropsch syntheses, in dehydrogenations of hydrocarbons, metathesis reactions, in the polygas method or other industrial processes. Furthermore, olefin mixtures comprising olefins of different carbon numbers can also be used for preparing alcohol mixtures.

In the inventive method, use can be made of all ester mixtures prepared from aromatic carboxylic acids and the above-mentioned alcohol mixtures. According to the invention, use is preferably made of esters prepared from phthalic acid, phthalic anhydride or benzoic acid and a mixture of isomeric alcohols having from 6 to 13 carbon atoms.

Examples of technical phthalates which can be used in the inventive method are the following products having the trade names:

Vestinol C (di-n-butyl phthalate) (CAS No. 84-74-2); Vestinol IB (diisobutyl phthalate) (CAS No. 84-69-5); Jayflex DINP (CAS No. 68515-48-0); Jayflex DIDP (CAS No. 68515-49-1); Palatinol 9P (68515-45-7), Vestinol 9 (CAS No. 28553-12-0); T (CAS No. 3319-31-1); Linplast 68-TM, Palatinol N (CAS No. 28553-12-0); Jayflex DHP (CAS No. 68515-50-4); Jayflex DIOP (CAS No. 27554-26-3); Jayflex UDP (CAS No. 68515-47-9); Jayflex DIUP (CAS No. 85507-79-5); Jayflex DTDP (CAS No. 68515-47-9); Jayflex L9P (CAS No. 68515-45-7); Jayflex L911P (CAS No. 68515-43-5); Jayflex L11P (CAS No. 3648-20-2); Witamol 110 (CAS No. 68515-51-5); Witamol 118 (di-n-C8-C10-alkyl phthalate) (CAS No. 71662-46-9); Unimoll BB (CAS No. 85-68-7); Linplast 1012 BP (CAS No. 90193-92-3); Linplast 13XP (CAS No. 27253-26-5); Linplast 610P (CAS No. 68515-51-5); Linplast 68 FP (CAS No. 68648-93-1); Linplast 812 HP (CAS No. 70693-30-0); Palatinol AH (CAS No. 117-81-7); Palatinol 711 (CAS No. 68515-42-4); Palatinol 911 (CAS No. 68515-43-5); Palatinol 11 (CAS No. 3648-20-2); Palatinol Z (CAS No. 26761-40-0); Palatinol DIPP (CAS No. 84777-06-0); Jayflex 77 (CAS No. 71888-89-6); Palatinol 10 P (CAS No. 533-54-0); Vestinol AH (CAS No. 117-81-7).

It must be noted that in the nuclear hydrogenation of aromatic di- or polycarboxylic acids or their esters from each isomer used, at least two stereoisomeric hydrogenation products can form. The mass ratios of the resultant stereoisomers to one another depend on the catalyst used and on the hydrogenation conditions. All hydrogenation products having any ratio(s) of the stereoisomers to one another can be used without separation, or else after a separation. Generally, the hydrogenation products are used without separation.

In the inventive method, solid hydrogenation catalysts are used which preferably comprise at least one metal of the first, seventh and/or eighth subgroup of the Periodic Table of the Elements, preferably at least one metal of the eighth subgroup of the Periodic Table of the Elements. Preferably, use is made of, in particular in the hydrogenation of aromatic carboxylic acids or their derivatives, as active metals of the eighth subgroup of the Periodic Table of the Elements, platinum, rhodium, palladium, cobalt, nickel or ruthenium, or a mixture of two or more thereof, in particular ruthenium being used as active metal.

In addition to the above-mentioned metals, in addition at least one metal of the first and/or seventh subgroup of the Periodic Table of the Elements may be present in the catalysts. Preferably, use is made of rhenium and/or copper.

The content of the active metals, i.e. of the metals of the first and/or seventh and/or eighth subgroup of the Periodic Table of the Elements, is preferably from 0.1 to 30% by mass. The noble metal content, i.e. of the metals of the eighth subgroup of the Periodic Table of the Elements and of the fifth or sixth period, e.g. palladium, ruthenium, calculated as metal, is preferably in the range from 0.1 to 10% by mass, in particular in the range from 0.8 to 5% by mass, very particularly between 1 and 3% by mass. Said contents of active metals are particularly preferred in particular in the hydrogenation of aromatic carboxylic acids or their derivatives.

Preferably, the catalysts used are supported catalysts. As supports, use can be made, for example, of the following materials: activated carbon, silicon carbide, aluminum oxide, silicon oxide, aluminosilicate, titanium dioxide, zirconium dioxide, magnesium oxide and/or zinc oxide or their mixtures. More preferably, use is made of a catalyst which has a titanium dioxide support. In addition, these support materials can comprise alkali metals, alkaline earth metals and/or sulfur.

In the inventive method, preferably use is made of ruthenium catalysts which are claimed in the patent documents DE 102 25 565.2 and DE 102 32 868.4.

In the inventive method, the hydrogenation units preferably each contain a hydrogenation reactor. This can be a tubular reactor, tube-bundle reactor, or preferably a shaft furnace.

The individual reactors can be operated adiabatically, polytropically or virtually isothermally, i.e. having a temperature increase of typically less than 10° C. In this case, in particular the reactors operated in the loop operating mode are preferably run quasiisothermally, preferably having a temperature increase less than 10° C., more preferably less than 5° C.

The inventive method, in particular in the hydrogenation of aromatic carboxylic acids or their derivatives, is carried out preferably in the liquid/gas mixed phase or liquid phase, in three-phase reactors in cocurrent flow, the hydrogenation gas being distributed in a manner known per se in the liquid starting material/product stream. In the interest of even liquid distribution, an improved removal of heat of reaction and/or a high space-time yield, the reactors operated in the loop operating mode are preferably run at high liquid loadings of from 10 to 400, preferably from 20 to 200, and more preferably from 40 to 150 m$^3$ per m$^2$ cross-sectional area of the empty reactor and hour.

The liquid loadings can be identical or different in the reactors operated in the loop operating mode. Preferably, the liquid loading is greatest in the first reactor and decreases in the subsequent reactors operated in loop operating mode. In a plant according to the invention having two series-connected loop reactors the liquid loading, in particular in the hydrogenation of aromatic carboxylic acids or their derivatives, in the first reactor is preferably in the range from 20 to 200, more preferably in the range from 40 to 150 m$^3$/(m$^2$·h) and in the second reactor, preferably in the range from 20 to 180, more preferably in the range from 40 to 140 m$^3$/(m$^2$·h). The loading of the reactor operated in the straight through-flow passage is preferably from 2 to 100 m$^3$/(m$^2$·h), more preferably from 10 to 80 m$^3$/(m$^2$·h).

The hydrogenation can be carried out in the absence, or preferably in the presence, of a solvent. As solvent, use can be made of all liquids which form a homogeneous solution with the starting material and product, which are inert under hydrogenation conditions and may readily be separated off from the product. The solvent can also be present in a mixture of a plurality of substances, and if appropriate water.

For the hydrogenation of aromatic carboxylic acids or their derivatives, use can be made, for example, of the following substances as solvent: straight-chain or cyclic ethers, for example tetrahydrofuran or dioxane and also aliphatic alcohols in which the alkyl radical has 1 to 13 carbon atoms. Alcohols which can preferably be used as solvents are isopropanol, n-butanol, isobutanol, n-pentanol, 2-ethylhexanol, nonanols, technical nonanol mixtures, decanol, technical decanol mixtures, tridecanols. The use of alcohols is only preferred when the compounds intended for hydrogenation are carboxylic esters. When alcohols are used as solvent, it can be expedient to use that alcohol or alcohol mixture which would be formed on saponification of the product. As a result, byproduct formation due to transesterification would be excluded. A further preferred solvent is the hydrogenation product itself.

By using a solvent, the aromatics concentration in the reactor feed can be limited, as a result of which better temperature control in the reactor can be achieved. This can have as consequence a minimization of side reactions and thus an increase in product yield. Preferably, the aromatics content in the reactor feed is between 1 and 70%. The desired concentration range can, in those reactors which are operated in the loop operating mode, be set by the circulation ratio (ratio of recirculated hydrogenation output to starting material). The aromatics concentration in the reactor feed (mixture of fresh starting material or hydrogenation output of the previous reactor and of circulation stream) preferably decrease from the first to the last reactor. For example, in a plant according to FIG. 1, the aromatics concentration in the feed to the first reactor (3) is in the range from 70 to 5% by mass, in the feed to the second reactor (11) in the range from 40 to 2% by mass, and in the feed to the third reactor (18) in the range from 20 to 1% by mass.

The inventive method is carried out, in particular in the hydrogenation of aromatic carboxylic acids or their derivatives, preferably in a pressure range from 0.3 to 30 MPa, in particular from 1.5 to 20 MPa, very particularly preferably from 5 to 20 MPa. The pressure in the individual reactors can be identical or different. Preferably, the pressures are identical or approximately identical.

The hydrogenation temperatures, in particular in the hydrogenation of aromatic carboxylic acids or their derivatives, are preferably from 50 to 250° C., more preferably from 80 to 200° C. The hydrogenation temperatures in individual reactors can be identical or different.

As products of the inventive method, corresponding compositions are obtained which are dependent on the starting materials and the conversion rate in the hydrogenation. The composition which is formed in the inventive hydrogenation of an aromatic carboxylic acid or its derivatives, in particular an aromatic di- or polycarboxylic ester or a mixture of aromatic di- or polycarboxylic esters by the inventive method has, when a pure aromatic carboxylic acid or its derivative is used, preferably a content of alicyclic carboxylic acids or their derivatives, in particular esters, of greater than 96% by mass, in particular greater than 98% by mass, very particularly preferably greater than 99% by mass. This mixture can be used directly or after purification. Byproducts can be separated off, for example by distillation, or by stripping with an inert gas such as nitrogen or steam. Preferably, small amounts of low boilers are separated off by stripping with steam in the temperature range from 120° C. to 240° C., in particular in the range from 150 to 200° C. and at a pressure of from 5 kPa to 10 kPa . Then, by reducing the pressure to below 5 kPa, the product can be dried.

Products which can be obtained by the inventive method, are, in particular mixtures and compositions which have alicyclic carboxylic acids and/or their derivatives, in particular alicyclic carboxylic esters, and particularly preferably alicyclic di- or polycarboxylic acids.

Another aspect of the present invention may be applied to a method for plasticizing plastics which comprises combining a compositions obtained by the inventive method with a plastic. That is, the present invention relates to the use of the inventively prepared alicyclic carboxylic acids and/or their derivatives, in particular ester-containing compositions, as plasticizers in plastics. Preferred plastics are PVC, homo- and copolymers based on ethylene, propylene, butadiene, vinyl acetate, glycidyl acrylate, glycidyl methacrylate, methacrylates, acrylates, acrylates having, bound to the oxygen atom of the ester group, alkyl radicals of branched or unbranched alcohols having one to ten carbon atom(s), styrene, acrylonitrile, homo- or copolymers of cyclic olefins.

As representatives of the above groups, the following plastics may be mentioned by way of example:

polyacrylates having identical or different alkyl radicals having 4 to 8 carbon atoms, bound to the oxygen atom of the ester group, in particular having the n-butyl, n-hexyl, n-octyl and 2-ethylhexyl radical and isononyl radical, polymethacrylate, polymethylmethacrylate, methylacrylate-butylacrylate copolymers, methylmethacrylate-butylmethacrylate copolymers, ethylene-vinylacetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers, methyl methacrylate-styrene-butadiene copolymers and/or nitrocellulose.

Furthermore, the inventively prepared alicyclic carboxylic esters can be used for modifying plastic mixtures, in particular for blending a polyolefin with a polyamide. Mixtures of plastics and the inventively prepared alicyclic polycarboxylic esters are likewise subject matter of the present invention. Suitable plastics are the abovementioned compounds. Such mixtures preferably comprise at least 5% by mass, particularly preferably 10-80% by mass, very particularly preferably 20-70% by mass, of the alicyclic polycarboxylic esters.

Mixtures of plastics, in particular PVC, which comprise one or more of the inventively prepared alicyclic polycarboxylic esters can, for example, be present in the following products, or be used for their preparation:

hoses, cables, wire sheathings, insulating tapes, in motor vehicle and furniture construction, plastisols, in floor coverings, medical articles, food packaging, seals, films, composite films, plates, artificial leather, toys, wallpaper, packaging vessels, adhesive tape films, clothing, coatings, coatings of textiles, shoes, underseal, seam seals, modeling compositions, or balls.

In addition to the abovementioned applications, the inventively prepared alicyclic carboxylic esters can be used as lubricating oil component, as constituent of cooling fluids and metal processing liquids. Likewise, they can be used as component in paints, varnishes, inks and adhesives.

The inventive method can be carried out in various embodiments. A preferred embodiment of the present invention is shown by way of example as a block diagram in the figure FIG. 1. This diagram has three reactors or reactor units of which two are operated in the loop operating mode. Of course, the inventive method can also be carried out using more than three reactors (or reactor units), or all three reactors can be operated in the loop operating mode.

In the variant of the inventive method according to FIG. 1, hydrogen (1a), starting material (2) and a part (8) of the liquid hydrogenation output (7) from the reactor (3) are fed into the hydrogenation unit (3). The hydrogenation output (4) from the hydrogenation unit (3) is separated in the phase separation vessel (5) into offgas (6) and liquid phase (7). A part (9) of the stream (7) is passed together with the part (16) of the liquid phase (15) from the second hydrogenation unit (11) and hydrogen (1b) into the hydrogenation unit (11). The hydrogenation output (12) from the hydrogenation unit (11) is separated in the phase separation vessel (13) into offgas (14) and liquid phase (15). A part (17) of the stream (15) is fed together with hydrogen (1c) into the hydrogenation unit (18). The hydrogenation output (19) from the hydrogenation unit (18) is separated in the phase separation vessel (20) into offgas (21) and crude product (22). Crude product (22) is either used as such or, after purification, in a plant which is not shown.

The present invention is described by way of example in the examples hereinafter, without the invention being intended to be limited to the embodiments specified in the examples.

EXAMPLES

In the examples hereinafter, the hydrogenation procedure is described, an end concentration of DINP in the output of the last stage of less than 0.05% of the input concentration in the first stage being intended to be achieved. In example 1, the hydrogenation was carried out using parameters which were obtained using catalyst volumes in the three stages which were obtained according to the invention by determining the minimum of the necessary total catalyst volume. In the comparative example (example 2), catalyst volumes were used which are obtained at a deviation of more than 20% from the minimum of the total catalyst volume determined.

The hydrogenation reactor is a tubular reactor and is operated continuously, optionally in straight through-flow passage, or in loop operating mode. In all experiments, the liquid phase and the hydrogenation gas flow cocurrently from top to bottom.

The tubular reactor is packed with 1350 ml of ruthenium catalyst (1% Ru/TiO$_2$). This catalyst is prepared from the TiO$_2$ support Aerolyst 7711 and an aqueous ruthenium nitrate solution as described in DE 102 32 868.4. The catalyst consists of cylindrical rod extrudates having the circle diameter of 1.5 mm and a length of 4 to 6 mm.

In both experiments, diisononyl phthalate, abbreviated form DINP, of Oxeno Olefinchemie GmbH having the trade name Vestinol 9 is used. As hydrogenation gas, use is made of hydrogen at a purity of greater than 99.9%.

In both examples the liquid hydrogenation output of one hydrogenation stage is the feed product of the next hydrogenation stage. The individual hydrogenation stages are carried out one after the other in the same reactor using the same catalyst and same catalyst quantity. The hydrogenation output of the first stage, after the quasisteady-state equilibrium is achieved, is collected and used for the second stage. In addition, the hydrogenation output of the second stage is collected as feed material for the third stage. For better comparability, the pressure, the reaction temperature and the offgas amount were identical in all hydrogenation steps.

Example 1

According to the Invention

The hydrogenation is carried out in three stages. In the first two stages, the reactor is operated in loop operating mode, and in the third stage in straight through-flow passage.

The operating parameters and the mass flow rates of Example 1 are compiled in Table 1.

TABLE 1

|  | 1st stage | 2nd stage | 3rd stage |
| --- | --- | --- | --- |
| Temperature (° C.) | 100 | 100 | 100 |
| Pressure (MPa) | 10 | 10 | 10 |
| Offgas (l(S.T.P.)/h) | 50 | 50 | 50 |
| Circulation rate (l/h) | 30 | 30 | 0 |
| Feed (l/h) | 9.54 | 3.18 | 1.05 |
| DINP concentration in the feed (%) (based on fresh DINP or hydrogenation output of the previous reactor) | 100 | 59.7 | 19.9 |
| Hydrogenation output (l/h)* | 9.592 | 3.197 | 1.053 |
| DINP concentration in the hydrogenation output (%) | 59.7 | 19.9 | <0.05 |
| LHSV (h$^{-1}$)** | 7.06 | 2.35 | 0.78 |

*Volume of the hydrogenation output, calculated assuming a density of 0.975 g/l and ignoring the offgas losses
**LHSV: liters of fresh DINP or liters of hydrogenation output from the previous reactor per liter of catalyst per hour.

The target product (hydrogenation output of the third stage) has a purity of greater than 99.5% by mass. The DINP conversion rate is virtually quantitative.

Taking into account the fact that the hydrogenation output of one stage is the feed material of the next stage, starting from 9.54 l/h of fresh DINP, for a continuous hydrogenation taking into account the differing densities of DINP and DINCH, gave the following feed streams (without recycle streams) to the reactors:

First reactor: 9.54 l/h
Second reactor: 9.592 l/h
Third reactor: 9.643 l/h

Maintaining the LHSV identified in table 1 gave, for the just mentioned volumetric flow rates, the following catalyst volumes:

First reactor: 1.35 l
Second reactor: 4.07 l
Third reactor: 12.36 l

The (total) catalyst volume in the two loop reactors corresponds accordingly to 5.42 l. For the overall hydrogenation, 17.78 l of catalyst are required. The feed of 9.54 l/h of fresh DINP to the first reactor, over the two loop reactors, gave a total LHSV of 1.75 h$^{-1}$.

Example 2

Comparison

The hydrogenation is carried out in three stages. In the first two stages, the reactor is operated in loop operating mode, and in the third stage in straight through-flow passage.

The operating parameters and the mass flow rates of Example 2 are compiled in Table 2.

TABLE 2

|  | 1st stage | 2nd stage | 3rd stage |
|---|---|---|---|
| Temperature (° C.) | 100 | 100 | 100 |
| Pressure (MPa) | 10 | 10 | 10 |
| Offgas (l(S.T.P.)/h) | 50 | 50 | 50 |
| Circulation rate (l/h) | 30 | 30 | 0 |
| Feed (l/h) | 9.54 | 1.28 | 1.20 |
| DINP concentration in the feed (%) (based on fresh DINP or hydrogenation output of the previous reactor) | 100 | 59.7 | 10.1 |
| Hydrogenation output (l/h)* | 9.592 | 1.29 | 1.20 |
| DINP concentration in the hydrogenation output (%) | 59.7 | 10.1 | <0.05 |
| LHSV (h$^{-1}$)** | 7.06 | 0.95 | 0.88 |

*Volume of the hydrogenation output, calculated assuming a density of 0.975 g/l and ignoring the offgas losses.
**LHSV: liters of fresh DINP or liters of hydrogenation output from the previous reactor per liter of catalyst per hour.

The target product (hydrogenation output of the third stage) has a purity of greater than 99.5% by mass. The DINP conversion rate is virtually quantitative.

Taking into account the fact that the hydrogenation output of one stage is the feed material of the next stage, starting from 9.54 l/h of fresh DINP, for a continuous hydrogenation taking into account the differing densities of DINM and DINCH, gave the following feed streams (without recycle streams) to the reactors:

First reactor: 9.54 l/h
Second reactor: 9.592 l/h
Third reactor: 9.643 l/h

Maintaining the LHSV identified in table 2 gave, for the just mentioned volumetric flow rates, the following catalyst volumes:

First reactor: 1.35 l
Second reactor: 10.09 l
Third reactor: 10.96 l

The (total) catalyst volume in the two loop reactors corresponded accordingly to 11.44 l. For the total hydrogenation, 22.4 l of catalyst are required. The feed of 9.54 l/h of fresh DINP to the first reactor, over the two loop reactors, gives a total LHSV of 0.43 h$^{-1}$.

As can be concluded from the results of example and comparative example, it is possible by means of the inventive method to determine the minimum necessary catalyst volume for hydrogenation reactions in two or more series-connected reactors without the total conversion rate being impaired.

The present application is based on German Patent Application No. 10 2004 063 673.7, filed in the German Patent Office on Dec. 31, 2004, and is hereby incorporated by reference in its entirety.

Obviously, numerous modifications and variations of the present invention are possible in light of the above teachings. It is therefore to be understood that within the scope of the appended claims, the invention may be practiced otherwise than as specifically described herein.

The invention claimed is:

1. A method for the continuous catalytic hydrogenation of at least one hydrogenatable compound using a hydrogenation gas in the presence of at least one solid catalyst disposed in a fixed bed, said method comprising:
carrying out the hydrogenation in at least three series-connected hydrogenation units, and
operating at least the first two hydrogenation units in loop operating mode, with, in the hydrogenation units, catalyst volumes being used which deviate by a maximum of 20% from the catalyst volumes which are obtained by a process which comprises
a) determining the kinetics of the hydrogenation to be carried out,
b) calculating the required catalyst volume for the reactor types used for preset reactor input and output concentrations,
c) determining the required total catalyst volume by combining the calculated catalyst volumes, in each case only those combinations being performed which lead to the desired end concentration of the starting material to be hydrogenated used,
d) preparing a curve from the total catalyst volumes determined in c) plotted against the conversion rate,
e) determining the minimum of the curve prepared in d), and
f) determining the catalyst volumes, of the individual hydrogenation units, to be assigned to the minimum,
wherein the at least one hydrogenatable compound is selected from the group consisting of
benzoic acid,
an ester of benzoic acid,
an anhydride of benzoic acid,
1-naphthoic acid,
an ester of 1-naphthoic acid,
an anhydride of 1-naphthoic acid,
2-naphthoic acid,
an ester of 2-naphthoic acid,
an anhydride of 2-naphthoic acid,
a dicarboxylic acid of benzene,
a mono-ester of a diarboxylic acid of benzene,
a bis-ester of a dicarboxylic acid of benzene,
an anhydride of a dicarboxylic acid of benzene,
a polycarboxylic acid of benzene,
a polycarboxylic acid of benzene that is partially esterified,
a polycarboxylic acid of benzene that is fully esterified,
an anhydride of a polycarboxylic acid of benzene,
a polycarboxylic acid of diphenyl,
a polycarboxylic acid of diphenyl that is partially esterified,
a polycarboxylic acid of diphenyl that is fully esterified,
an anhydride of a polycarboxylic acid of diphenyl,
a polycarboxylic acid of naphthalene,
a polycarboxylic acid of naphthalene that is partially esterified,
a polycarboxylic acid of naphthalene that is fully esterified,
an anhydride of a polycarboxylic acid of naphthalene,
a polycarboxylic acid of diphenyl oxide,
a polycarboxylic acid of diphenyl oxide that is partially esterified,
a polycarboxylic acid of diphenyl oxide that is fully esterified,
an anhydride of a polycarboxylic acid of diphenyl oxide,
a polycarboxylic acid of anthracene,
a polycarboxylic acid of anthracene that is partially esterified,
a polycarboxylic acid of anthracene that is fully esterified,
an anhydride of a polycarboxylic acid of anthracene,
and combinations thereof.

2. The method as claimed in claim 1, wherein all hydrogenation units are operated in loop operating mode.

3. The method as claimed in claim 1, wherein the last hydrogenation unit is operated in straight through-flow passage.

4. The method as claimed claim 1, wherein the at least one solid catalyst comprises at least one metal of the eighth subgroup of the Periodic Table of the Elements.

5. The method as claimed in claim 4, wherein the at least one solid catalyst comprises ruthenium.

6. The method as claimed in claim 1, wherein the at least one solid catalyst comprises a titanium dioxide support.

7. The method of claim 1, wherein the at least one hydrogenatable compound is selected from the group consisting of
a dicarboxylic acid of benzene,
a mono-ester of a diarboxylic acid of benzene,
a bis-ester of a dicarboxylic acid of benzene,
an anhydride of a dicarboxylic acid of benzene,
a polycarboxylic acid of benzene,
a polycarboxylic acid of benzene that is partially esterified,
a polycarboxylic acid of benzene that is fully esterified,
an anhydride of a polycarboxylic acid of benzene,
a polycarboxylic acid of diphenyl,
a polycarboxylic acid of diphenyl that is partially esterified,
a polycarboxylic acid of diphenyl that is fully esterified,
an anhydride of a polycarboxylic acid of diphenyl,
a polycarboxylic acid of naphthalene,
a polycarboxylic acid of naphthalene that is partially esterified,
a polycarboxylic acid of naphthalene that is fully esterified,
an anhydride of a polycarboxylic acid of naphthalene,
a polycarboxylic acid of diphenyl oxide,
a polycarboxylic acid of diphenyl oxide that is partially esterified,
a polycarboxylic acid of diphenyl oxide that is fully esterified,
an anhydride of a polycarboxylic acid of diphenyl oxide,
a polycarboxylic acid of anthracene,
a polycarboxylic acid of anthracene that is partially esterified,
a polycarboxylic acid of anthracene that is fully esterified,
an anhydride of a polycarboxylic acid of anthracene,
and combinations thereof 8. The method of claim 1, wherein the at least one hydrogenatable compound is selected from the group consisting of
benzoic acid,
an ester of benzoic acid,
an anhydride of benzoic acid,
1-naphthoic acid,
an ester of 1-naphthoic acid,
an anhydride of 1-naphthoic acid,
2-naphthoic acid,
an ester of 2-naphthoic acid,
an anhydride of 2-naphthoic acid,
and combinations thereof.

9. The method of claim 1, wherein the at least one hydrogenatable compound is selected from the group consisting of
an ester of benzoic acid,
an ester of 1-naphthoic acid,
an ester of 2-naphthoic acid,
a mono-ester of a diarboxylic acid of benzene,
a bis-ester of a dicarboxylic acid of benzene,
a polycarboxylic acid of benzene that is partially esterified,
a polycarboxylic acid of benzene that is fully esterified,
a polycarboxylic acid of diphenyl that is partially esterified,
a polycarboxylic acid of diphenyl that is fully esterified,
a polycarboxylic acid of naphthalene that is partially esterified,
a polycarboxylic acid of naphthalene that is fully esterified,
a polycarboxylic acid of diphenyl oxide that is partially esterified,
a polycarboxylic acid of diphenyl oxide that is fully esterified,
a polycarboxylic acid of anthracene that is partially esterified,
a polycarboxylic acid of anthracene that is fully esterified,
and combinations thereof.

10. The method as claimed in claim 9, wherein the alcohol components of each ester present in the at least one hydrogenatable compound have branched or unbranched alkoxyalkyl, cycloalkyl and/or alkyl groups having 1 to 25 carbon atoms.

11. The method as claimed in claim 9, wherein the alcohol components of the aromatic di- and/or polycarboxylic esters are in each case identical or different.

12. The method of claim 1, comprising the bis-ester of a dicarboxylic acid of benzene, wherein the bis-ester of the dicarboxylic acid of benzene is diisononyl phthalate or didecyl phthalate.

13. The method as claimed in claim 8, comprising the ester of benzoic acid, wherein the ester of benzoic acid comprises isononyl benzoate or decyl benzoate.

14. The method as claimed in claim 1, wherein for the loop reactors, the catalyst volumes deviate by a maximum of 5% from the determined catalyst volumes.

* * * * *